(12) United States Patent
Chou et al.

(10) Patent No.: US 8,813,539 B2
(45) Date of Patent: Aug. 26, 2014

(54) ELECTROCHEMISTRY APPARATUS

(75) Inventors: Chen-Chia Chou, Taipei (TW); Tsung-Her Yeh, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 673 days.

(21) Appl. No.: 13/089,199

(22) Filed: Apr. 18, 2011

(65) Prior Publication Data

US 2011/0192718 A1 Aug. 11, 2011

Related U.S. Application Data

(63) Continuation-in-part of application No. 12/168,338, filed on Jul. 7, 2008, now Pat. No. 8,016,988.

(30) Foreign Application Priority Data

Jul. 10, 2007 (TW) ................ 96125048 A

(51) Int. Cl.
  *G01K 7/02* (2006.01)
  *G01N 7/18* (2006.01)
  *G01N 25/00* (2006.01)
  *G01N 27/407* (2006.01)

(52) U.S. Cl.
  CPC .......... *G01N 27/407* (2013.01); *G01N 27/4073* (2013.01)
  USPC ......... 73/23.32; 73/25.05; 374/141; 374/179; 429/480; 204/424

(58) Field of Classification Search
  USPC ......... 374/141, 142, 144, 163, 100, 164, 179, 374/43–45; 205/782
  See application file for complete search history.

(56) References Cited

U.S. PATENT DOCUMENTS

| | | | | | |
|---|---|---|---|---|---|
| 4,356,065 | A | * | 10/1982 | Dietz | 205/783 |
| 4,724,061 | A | * | 2/1988 | Nyberg | 204/412 |
| 4,957,705 | A | * | 9/1990 | Uchikawa | 422/94 |
| 5,246,792 | A | * | 9/1993 | Watanabe | 429/492 |
| 5,393,397 | A | * | 2/1995 | Fukaya et al. | 204/424 |
| 5,635,039 | A | * | 6/1997 | Cisar et al. | 204/252 |
| 7,169,367 | B2 | * | 1/2007 | Takeyama et al. | 422/198 |
| 7,306,708 | B2 | * | 12/2007 | Okuno | 204/425 |
| 8,012,325 | B2 | * | 9/2011 | Oya et al. | 204/429 |
| 8,465,636 | B2 | * | 6/2013 | Sugaya et al. | 204/429 |
| 2001/0025789 | A1 | * | 10/2001 | Miyashita et al. | 204/431 |
| 2002/0104758 | A1 | * | 8/2002 | Mizutani et al. | 204/427 |

(Continued)

FOREIGN PATENT DOCUMENTS

JP 2009281973 A * 12/2009
WO WO 9428403 A1 * 12/1994

*Primary Examiner* — Gail Verbitsky

(57) ABSTRACT

An electrochemistry apparatus comprises a supporting body and a reaction layer for generating electromotive force. The supporting body is made of a first material. The reaction layer covers the surface of the supporting body and comprises an ion conductive layer, a first film electrode and a second film electrode. The first and the second film electrodes are separately formed on two opposite surfaces of the ion conductive layer. The ion conductive layer is made of a second material having a thermal expansion coefficient approximating to the thermal expansion coefficient of the first material. The second material has an ionic conductivity greater than the ionic conductivity of the first material. The first material has a toughness greater than the second material. The electrochemistry apparatus employs the supporting body with improved toughness and the ion conductive layer with improved ion conductivity, so as to increase sensitivity and thermal shock resistance.

16 Claims, 8 Drawing Sheets

(56) References Cited

U.S. PATENT DOCUMENTS

| | | | |
|---|---|---|---|
| 2002/0108856 A1* | 8/2002 | Kunimoto et al. | 204/425 |
| 2002/0108872 A1* | 8/2002 | Symons et al. | 205/784 |
| 2003/0066763 A1* | 4/2003 | Watanabe et al. | 205/792.5 |
| 2003/0121801 A1* | 7/2003 | Inaba et al. | 205/785.5 |
| 2003/0190508 A1* | 10/2003 | Takeyama et al. | 429/20 |
| 2003/0205078 A1* | 11/2003 | Hasei et al. | 73/23.31 |
| 2004/0045823 A1* | 3/2004 | Kawase et al. | 204/424 |
| 2004/0118683 A1* | 6/2004 | Watanabe et al. | 204/424 |
| 2005/0016841 A1* | 1/2005 | Chang et al. | 204/280 |
| 2005/0173264 A1* | 8/2005 | Reitmeier et al. | 205/783.5 |
| 2006/0237316 A1* | 10/2006 | Clyde et al. | 204/424 |
| 2006/0283708 A1* | 12/2006 | Ando et al. | 204/424 |
| 2007/0054170 A1* | 3/2007 | Isenberg | 429/33 |
| 2007/0080075 A1* | 4/2007 | Wang et al. | 205/781 |
| 2007/0125664 A1* | 6/2007 | LaBarge et al. | 205/780.5 |
| 2007/0245803 A1* | 10/2007 | Tan et al. | 73/31.05 |
| 2008/0085440 A1* | 4/2008 | Yasumoto et al. | 429/30 |
| 2008/0107923 A1* | 5/2008 | Wallace et al. | 429/8 |
| 2009/0013761 A1* | 1/2009 | Chou et al. | 73/31.05 |
| 2010/0297479 A1* | 11/2010 | Tsuchida et al. | 429/49 |
| 2013/0285682 A1* | 10/2013 | Biskupski et al. | 324/693 |

* cited by examiner

ELECTROCHEMISTRY APPARATUS

CROSS REFERENCE TO RELATED APPLICATIONS

This application is a continuation-in-part of U.S. patent application Ser. No. 12/168,338 filed on Jul. 7, 2008, which claims priority of Taiwan Patent Application No. 096125048, filed on Jul. 10, 2007, the entirety of which is incorporated by reference herein.

BACKGROUND OF THE INVENTION

1. Field of the Invention

The present invention relates to an electrochemistry apparatus, and in particular relates to an electrochemistry apparatus made of the ceramic material with high toughness and high ion conductivity.

2. Description of the Related Art

FIG. 1 shows a conventional oxygen sensor 10 comprising a first electrode 11, a second electrode 12, a chamber 13, a ceramic body 14 and a gas selective layer 15. The chamber 13 is formed in a center of the ceramic body 14. A first electrode 11 is formed on an inner wall of the chamber 13. The second electrode 12 is formed on an outer wall of the ceramic body 14. The gas selective layer 15 is coated on the second electrode 12. In gas detection, the chamber 13 is connected to an environmental gas, the environment gas reacts with the first electrode 11, and a gas to be measured passes the gas selective layer 15 to react with the second electrode 12. The oxygen consistency of the environmental gas differs from that of the gas to be measured. Thus, a voltage difference is formed between the first electrode 11 and the second electrode 12. The voltage difference generates an electromotive force to conduct the first electrode 11 and the second electrode 12 through the ceramic body 14. The oxygen consistency of the gas to be measured is obtained by measuring the voltage difference.

Conventionally, the ion conductive layer 14 is made by an injection, a dry press or an extrusion process. A conventional ion conductive layer 14 is thick with minimal sensitivity and high costs.

In the environment for testing the gas sensor 10, especially in high temperature environment, the thermal shock results in the degradation of the ceramic body 14 easily, which cause the gas sensor 10 decrease in operating lifespan and decline in function. Most of the gas sensors are shaped as a post or a plane. For example, the gas sensor disclosed in U.S. Pat. No. 6,797,138 has a structure of stacking multilayer, and is made by tape-casting or sheet thermal superimposition. The process of thermal treatment and sintering causes the gas sensor 10 warping or cracking due to the uneven contraction in different parts. US patent publication No. 2007012566A1 discloses a multilayer tubular sensor applied to detecting NiOx. The conventional multilayer tubular sensor is also fabricated by tape-casting or sheet thermal superimposition. However, the mechanical strength such as toughness or bending strength of the multilayer tubular sensor is insufficient.

BRIEF SUMMARY OF THE INVENTION

A detailed description is given in the following embodiments with reference to the accompanying drawings.

An electrochemistry apparatus is provided. The electrochemistry apparatus comprises a supporting body and a reaction layer for generating electromotive force. The supporting body is made of a first material and has a surface. The reaction layer covers the surface of the supporting body and comprises an ion conductive layer, a first film electrode and a second film electrode. The ion conductive layer comprises a first surface and a second surface, wherein the first surface is opposite to the second surface. The ion conductive layer is made of a second material, wherein the second material has a thermal expansion coefficient which approximates the thermal expansion coefficient of the first material, the second material has an ionic conductivity which is greater than the ionic conductivity of the first material, and the first material has a toughness which is greater than the second material. The first film electrode is formed on the first surface. The second film electrode is formed on the second surface and located corresponding to the first film electrode.

In above embodiment, the supporting body may be made of ceramic material with better mechanical properties, such as combined material with cermet or metal to increase bending strength and toughness. The ion conductive layer can be made of ceramic material with high ion conductivity. Because the supporting body and the ion conductive layer have approximate thermal expansion coefficients, the electrochemistry apparatus increases the thermal shock resistance to reduce the warping or cracking. In an embodiment, the supporting body has a symmetrical shape, so that the surface of the supporting body is easier covered by the ion conductive layer. The ion conductive layer and the two film electrodes may be formed by a thick film process or a thin film process. Thus, the thickness of the reaction layer is reduced, and sensitivity thereof is increased.

The electrochemistry apparatus of the invention incorporates the improved structure with the improved materials of the supporting body and the ion conductive layer, so as to increase sensitivity, thermal shock resistance and operating lifespan, and reduce cost and material consumption when compared with conventional gas sensors.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
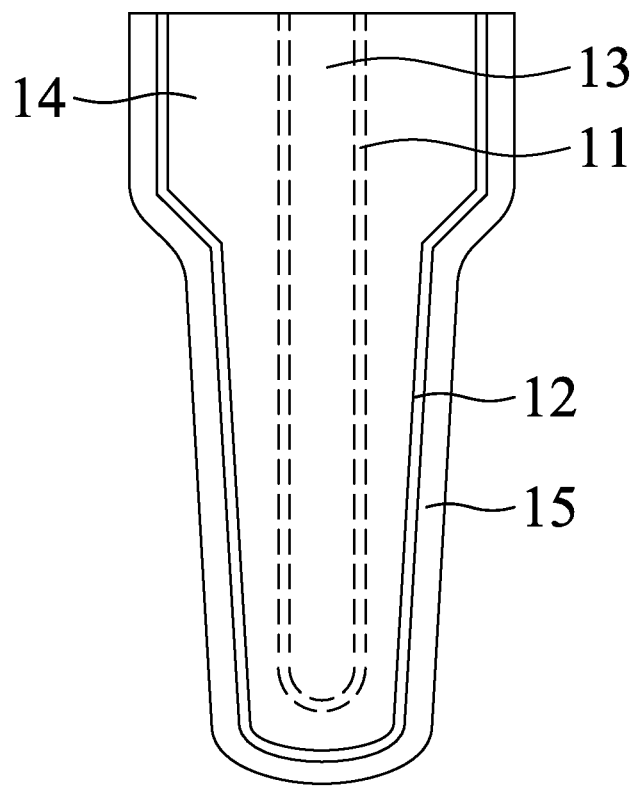
FIG. 1 shows a conventional oxygen sensor.
Figure 2:
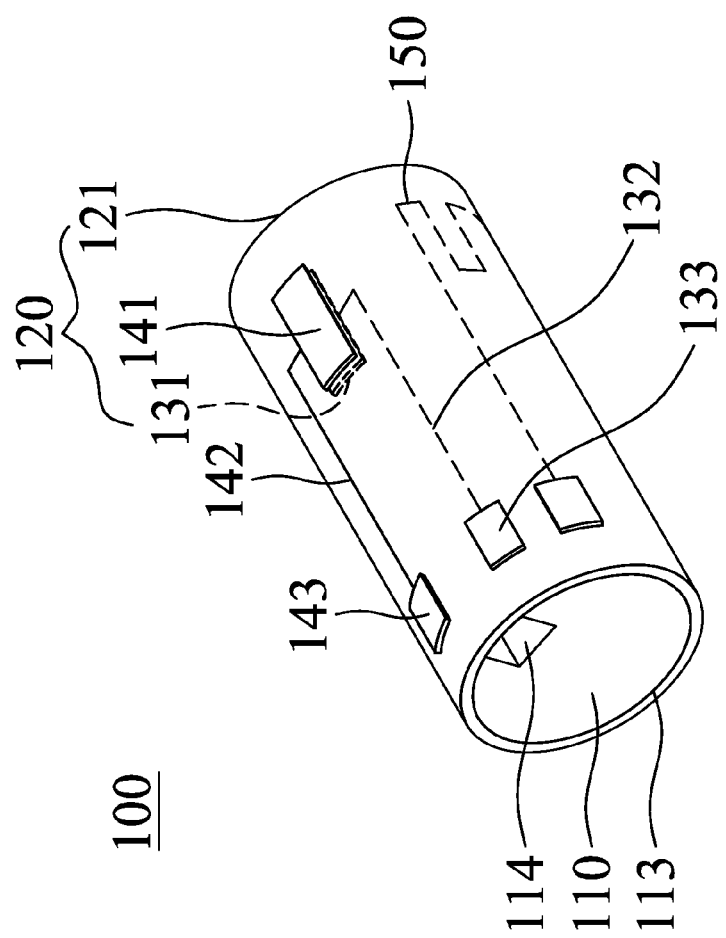
FIG. 2 shows an electrochemistry apparatus of a first embodiment of the invention.

FIG. 2 shows an electrochemistry apparatus 100 of a first embodiment of the invention, comprising a supporting body 110 and a reaction layer 120 for generating electromotive force. The supporting body 110 is made of a first material and has a side surface 113. Preferably, the supporting body 110 has a symmetrical shape such as a cylinder, a cube or a post with a cross-section of regular polygon. The reaction layer 120 covers the side surface 113 of the supporting body 110 and comprises an ion conductive layer 121, a first film electrode 131 and a second film electrode 141. Preferably, the reaction layer 120 further comprises a heating element 150.

It is worth noting that the ion conductive layer 121 is made of a second material which has a thermal expansion coefficient which approximates the thermal expansion coefficient of the first material of the supporting body 110. The second material of the ion conductive layer 121 has an ionic conductivity which is greater than the ionic conductivity of the first material of the supporting body 110, and the first material has a toughness which is greater than the toughness of the second material.

For example, the supporting body 110 is made of a combined material including a ceramic based material with an additive capable of enhancing the mechanical properties such as bending strength and the toughness. The ion conductive layer 121 can be made of a combined material including the same ceramic based material with a dopant capable of enhancing ion conductivity. Therefore, the electrochemistry apparatus 100 can resist thermal shock to reduce warping or cracking because the supporting body 110 and the ion conductive layer 121 have approximate thermal expansion coefficient. Furthermore, the electrochemistry apparatus 100 increases the mechanical strength and the ion conductivity thereof because of the improvement in material properties of the supporting body 110 and the ion conductive layer 121.

The above concept of the invention can be employed in solid oxide fuel cells (SOFC) and oxygen gas sensors. Take the structure of oxygen gas sensor as an example in the following embodiments, the supporting body 110 comprises a groove 114. The groove 114 is formed on the side surface 113 of the supporting body 110. The ion conductive layer 121 covers the side surface 113 of the supporting body 110. The ion conductive layer 121 comprises a first surface and a second surface. The second surface is opposite to the first surface. The ion conductive layer 121 and the groove 114 compose a chamber. The first film electrode 131 is formed on the first surface. The second film electrode 141 is formed on the second surface. The second film electrode 141 is located corresponding to the first film electrode 131. The first film electrode 131 is located in the chamber.

During gas detection, the chamber (composed of by the groove 114 and the ion conductive layer 121) is connected to an environmental gas. The environment gas reacts with the first film electrode 131. A gas to be measured contacts the second film electrode 141, and reacts with the second film electrode 141. The oxygen concentration of the environmental gas differs from that of the gas to be measured. Thus, the oxygen concentration difference generates an electromotive force, and a voltage difference is formed between the first film electrode 131 and the second film electrode 141. The oxygen concentration of the gas to be measured is obtained by measuring the voltage difference.

In the first embodiment of the invention, the supporting body 110 supports the ion conductive layer 121. The supporting body 110 has a symmetrical shape to increase the mechanical strength of the ceramic green body thereof, so that the ion conductive layer 121 can cover the supporting body 110 more easily or can be formed on the supporting body 110 by a thick film or a thin film process. Thus, the thickness of the ion conductive layer 121 is reduced, and sensitivity thereof is increased. To sum up, the electrochemistry apparatus 100 of the invention incorporates the improved structure with the improved materials of the supporting body and the ion conductive layer, so as to increase sensitivity, thermal shock resistance and operating lifespan, and reduce cost and material consumption when compared with conventional gas sensors.

Figure 3A:
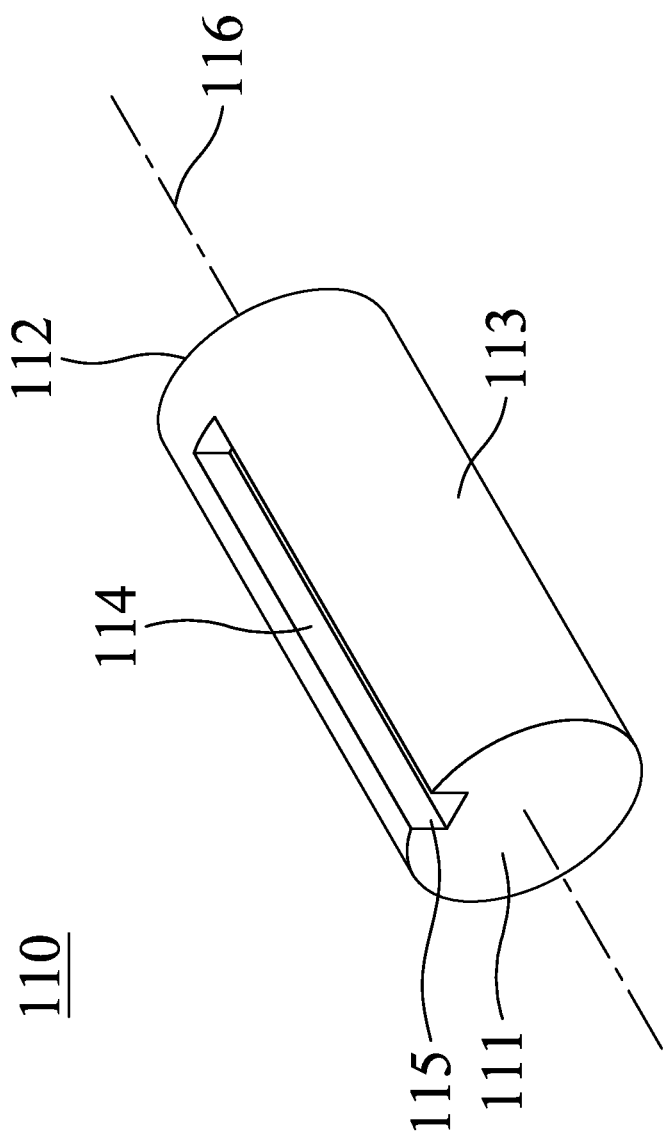
FIG. 3a shows a detailed structure of the supporting body.
Figure 3B:
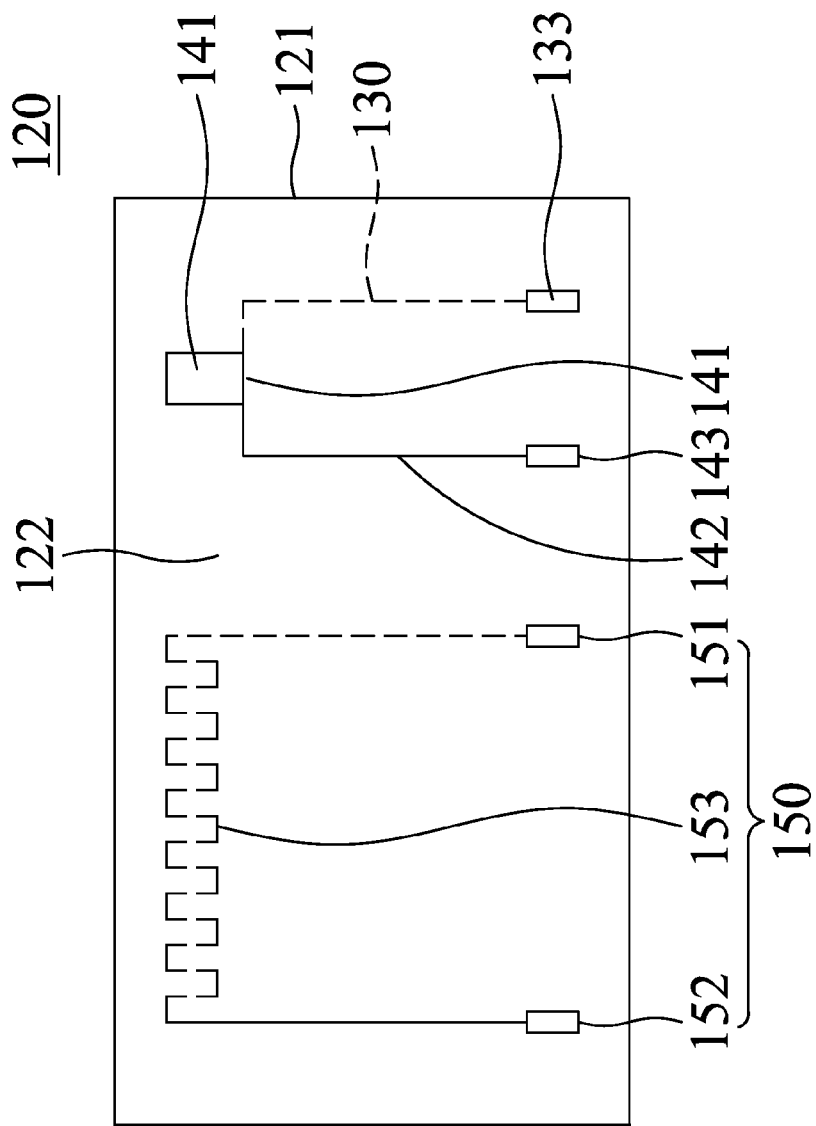
FIG. 3b is a top view of the ion conductive layer.
Figure 3C:
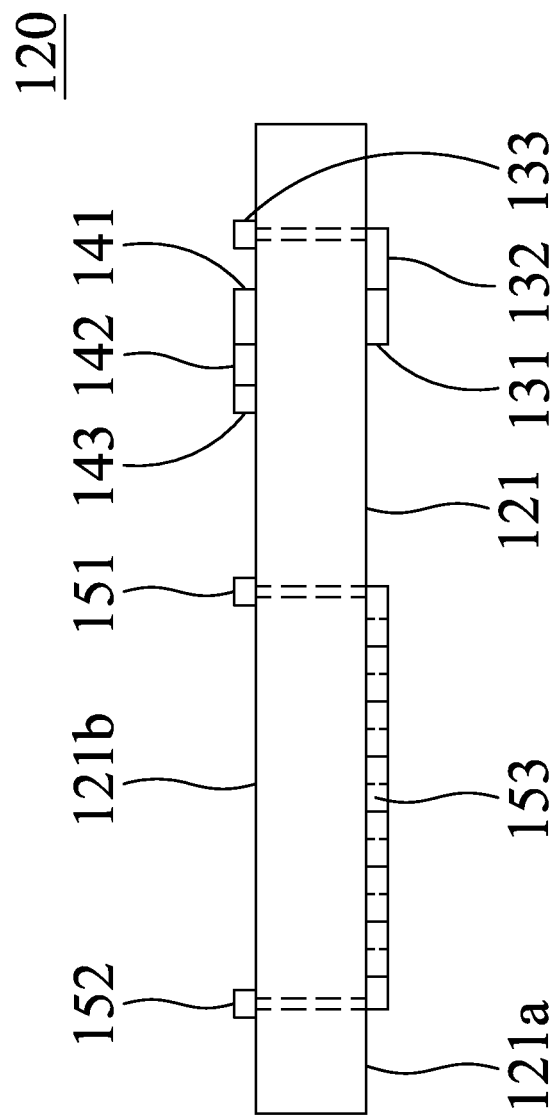
FIG. 3c is a side view of the ion conductive layer.

FIGS. 3a to 3c show a detailed structure of the electrochemistry apparatus 100. With reference to FIG. 3a, the supporting body 110 is a cylinder symmetric around a major axis 116. The cylinder comprises a first end 111, a second end 112, the side surface 113 and the groove 114. The groove 114 is formed on the side surface 113. An opening 115 is formed on the first end 111, and connected to the groove 114. The groove 114 extends parallel to a major axis 116 of the supporting body 110. In the embodiment, the groove 114 does not contact the second end 112. A minimum cross-section area of the groove is 1 mm$^2$. In another embodiment, there are plural grooves 114 symmetrically located on the surface of the supporting body 110 with respect to the major axis 116.

The supporting body 110 is made of a structural ceramic or an electronic ceramic, such as a zirconium oxide base (3Y-TZP+YNbO$_4$ system 18 Mpa/m$^{1/2}$), a zirconium oxide base with aluminum oxide (hominess phase), a cerium oxide base with aluminum oxide (hominess phase), a Perovskite (ABO$_3$) with aluminum oxide (hominess phase) or a tungsten carbide cermet with zirconium oxide to provide tenacity. In an embodiment, the material of the supporting body 110 has a toughness of greater than about 5.1 Mpa/m$^{1/2}$, preferably in the range from 5.1 to 18 Mpa/m$^{1/2}$. The supporting body 110 can be formed by a slip casting, a press molding, an (heat) injection printing or an injection process. The supporting body 110 of the embodiment has a simple structure, and can be mass produced to decrease costs.

The ion conductive layer 121 can comprise cerium oxide, zirconium oxide doped with positive ion with +2 charges, zirconium oxide doped with positive ion with +3 charges, or zirconium oxide co-doped with positive ion with +2 and +3 charges. The ion-conductive material, proton-conductive material or electron-conductive material can also be LaMo$_2$O$_9$, Perovskite or Ga—Mg—Sr—La oxides. In an embodiment, the material of the ion conductive layer 121 has an ion conductivity of greater than about 0.015 S/cm at 800° C., preferably in the range from 0.015 to 0.022 S/cm at 800° C. The ion conductive layer 120 can be formed by a thick film process, such as a screen print, a dry press, an injection printing, a scrape, a spreading or an immersion plating process. The ion conductive layer 120 can also be formed by a thin film process of Micro Electro-Mechanical Systems, such as a lift-off process.

With reference to FIGS. 3b and 3c, the conductive layer 121 comprises a first surface 121a and a second surface 121b. The second surface 121b is opposite to the first surface 121a. The first film electrode 131 is formed on the first surface 121a. The second film electrode 141 is formed on the second surface 121b, and located corresponding to the first film electrode 131. The heating element 150 comprises a first contact 151, a second contact 152 and a heating wire 153. The first contact 151 and the second contact 152 are formed on the second surface 121b. The heating wire 153 is disposed in the ion conductive layer 121 or in the supporting body 110, or disposed on the surface of the ion conductive layer 120 or the supporting body 110. To get the optimum stress distribution, when the heating wire 153 covers the side surface 113 of the supporting body 110, the ratio of the area covered by the heating wire 153 to the area covered by both the first and the second film electrodes 131, 141 is in the range of 1:1 to 3:1. Preferably, when the reaction layer 120 lapped the supporting body 110, the heating wire 153 and the two film electrodes 131, 141 overlap.

The electrochemistry apparatus 100 further comprises a first signal transmission point 133, a first conductive wire 132, a second signal transmission point 143 and a second conductive wire 142. The first conductive wire 132 is electrically connected to the first film electrode 131 and the first signal transmission point 133. The second conductive wire 142 is electrically connected to the second film electrode 141 and the second signal transmission point 143. With reference to FIG. 2, the first signal transmission point 133 and the second signal transmission point 143 are separately corresponding to two sides of the groove 114. The first conductive wire 132 is connected to the first signal transmission point 133 on the second surface 122 via the through hole.

Both the first film electrode 131 and the second film electrode 141 may be made of a complex material which incorporates a catalyzer with the same material as the ion conductive layer. In an embodiment, the first and second film electrodes 131, 141 can comprise the following materials: (a) metal materials such as Pt, Au, Pd, Rh, Ir, Ru, Os, Ni, Co and Fe which can easily electrical-chemical react with oxygen; (b) Perovskite ceramics such as $LaSrMnO_3$ and $LaSrCoFeO_3$, which can easily electrical-chemical react with oxygen; (c) a combined material comprising the metal materials mixed with the Perovskite ceramics mentioned above with zirconium oxide to provide ion-conduction and electron-conduction; and (d) a second phase material for resisting carbonization, poisoning or vulcanization, such as copper or cerium oxide. The first and second catalyzer layers can be formed by a thick film process, such as a screen print, an injection print, a spread or an immersion plating process. The first and second catalyzer layers can also be formed by a thin film process, such as a lift-off process.

The heating wire 153 may be made of the following materials: (a) metal materials such as Pt, Au, Pd, Rh, Ir, Ru, Os, Ni, Co and Fe which can easily electrical-chemical react with oxygen; (b) Perovskite ceramics such as $LaSrMnO_3$ and $LaSrCoFeO_3$; (c) a combined material comprising the metal materials and the Perovskite ceramics mentioned above. To match well between the heating wire 153 and the supporting body 110 or between the heating wire 153 and the ion conductive layer 121, the material of the heating wire 153 comprises an additive, and the additive is the same as a major composition of the supporting body 110 or the ion conductive layer 121, such as zirconium oxide.

Figure 4:
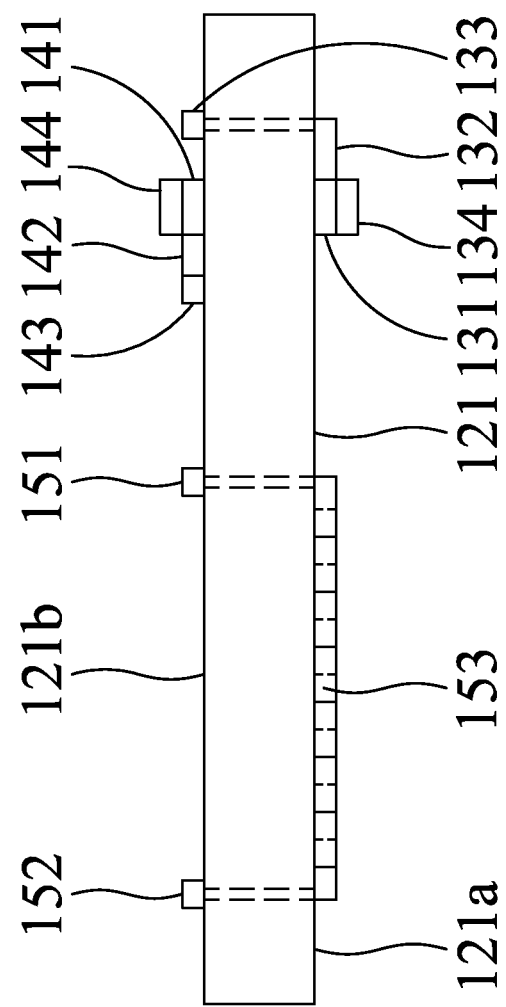
FIG. 4 shows the first embodiment comprising a gas diffusion layer.

With reference to FIG. 4, in a modified embodiment of the invention, a first gas diffusion layer 134 is formed on a surface of the first film electrode 131, and a second gas diffusion layer 144 is formed on a surface of the second film electrode 141. The first and second gas diffusion layers 134, 144 can comprise (a) hexagonal prism porous material, such as $LaAl_{11}O_8$ or $LaAlO_3$, or (b) magnesium aluminate spinel. The first and second gas diffusion layers 134, 144 can be formed by a thick film process, such as a screen print, a dry press, a scrape, an injection print, a spread or an immersion plating process. The first and second catalyzer layers can also be formed by a thin film process, such as a lift-off process. Preferably, the proportion of $LaAl_{11}O_8$ in the material of the gas diffusion layers 134, 144 is in the range from 50 to 100 mol %. The void ratio of the gas diffusion layers 134, 144 is in the range from 20 to 65%.

In above embodiments, it is worth noting that different fabrication processes result in different microcosmic structure or phase distribution of the ceramic element such as supporting body 110 and ion conductive layer 121. The average temperature varies with the sintering process for combination of different materials. A two-step sintering process is employed to avoid other combined phase generated from transient liquid phase sintering. The first step includes shaping the ceramic based material and additives for enhancing the ion conductive and/or mechanical strength into the elements, such as supporting body, ion conductive layer or the heating wire, by performing composition control of materials in milled powder mixture, and then calcining to form a desired phase structure. The second step includes forming the best diffusion path of oxygen ions and the best density in the shaped elements by ventilating via hot-press, hot-isostatic-press, electric furnace or atmosphere furnace, performing thermal treatment at 750° C.~1600° C., and then co-sintering.

Figure 5:
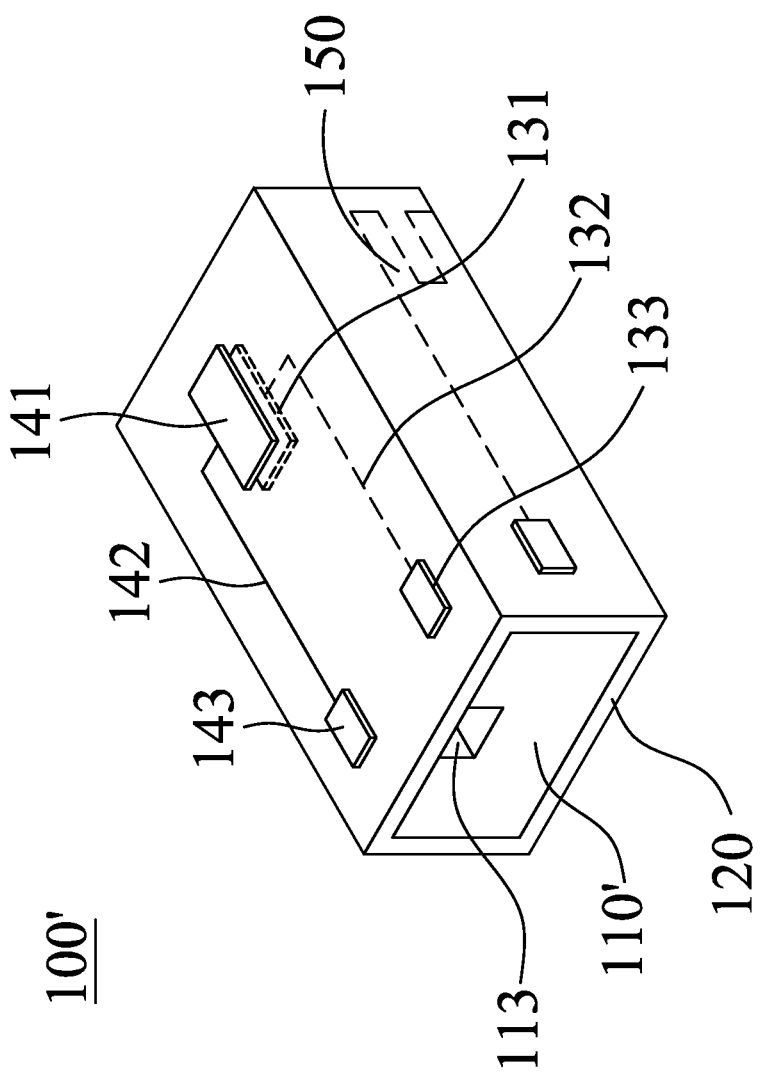
FIG. 5 shows an electrochemistry apparatus of a modified embodiment of the first embodiment of the invention.

FIG. 5 shows an electrochemistry apparatus 100' of a modified embodiment of the first embodiment of the invention, wherein the supporting body 110' is a cube. In the invention, the shape of the supporting body can be modified. Note that the embodiments do not limit the invention.

Figure 6:
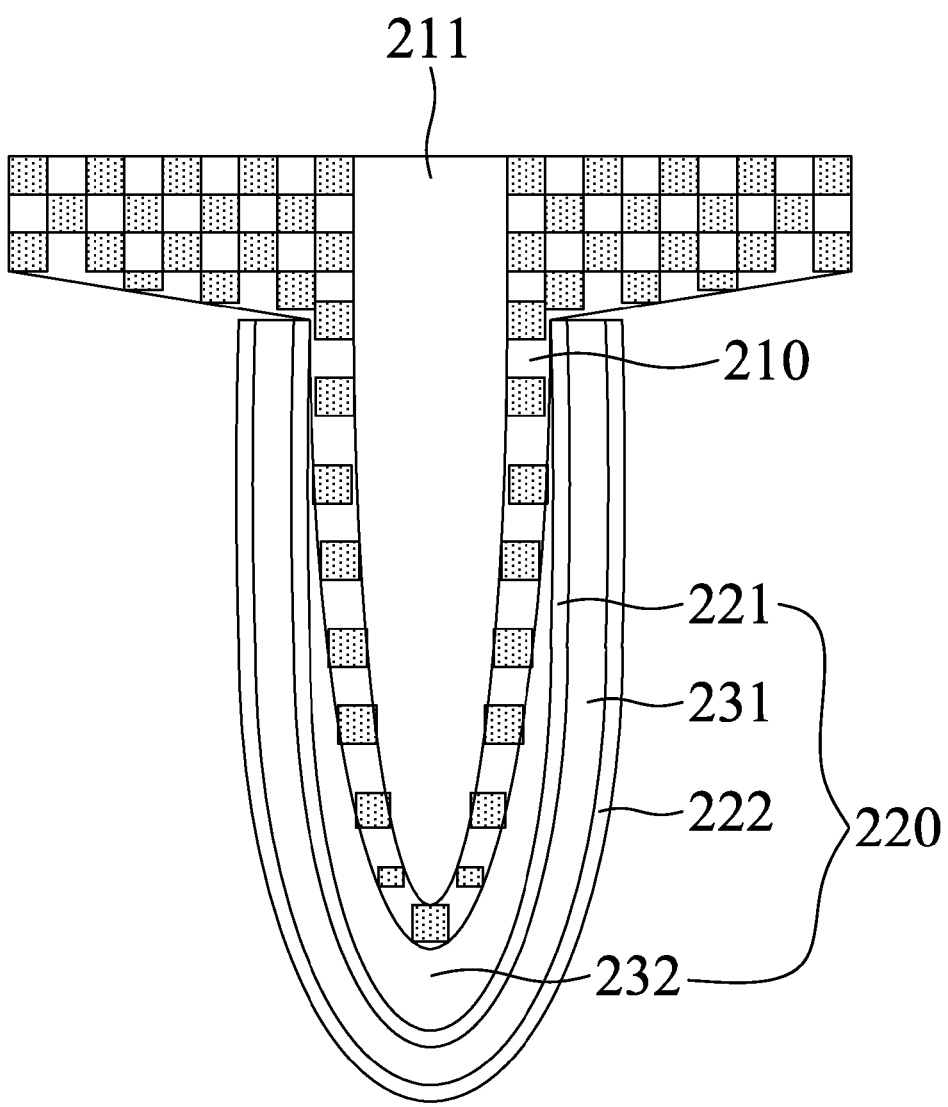
FIG. 6 shows an electrochemistry apparatus of a second embodiment of the invention.

FIG. 6 shows an electrochemistry apparatus 200 of a second embodiment of the invention, comprising a supporting body 210 and a reaction layer 220 for generating electromotive force. The reaction layer 220 comprises a first film electrode 221, a second film electrode 222, a first ion conductive layer 231 and a second ion conductive layer 232. The supporting body 210 comprises a chamber 211. The supporting body 210 is formed by a porous material with a toughness which is greater than the toughness of the material of the ion conductive layers 231 and 232. The materials of the ion conductive layers 231 and 232 have each an ionic conductivity which is greater than the ionic conductivity of the material of the supporting body 210. It is worth noting that the materials of the ion conductive layers 231 and 232 have a thermal expansion coefficient which approximates the thermal expansion coefficient of the material of the supporting body 210.

The second ion conductive layer 232 is coated on an outer surface of the supporting body 210. The first electrode 221 is coated on an outer surface of the second ion conductive layer 232. The first ion conductive layer 231 is coated on an outer surface of the first electrode layer 221. The second electrode layer 222 is coated on an outer surface of the first ion conductive layer 231. The first ion conductive layer 231 is sandwiched between the first film electrode 221 and the second film electrode 222.

During detection, the chamber 211 is connected to an environmental gas, the environmental gas passes the supporting body 210 and the second ion conductive layer 232 to react with the first film electrode 221, and a gas to be measured contacts the second film electrode 222 to react therewith. The oxygen concentration of the environmental gas differs from that of the gas to be measured. Thus, the oxygen concentration difference generates an electromotive force, and a voltage difference is formed between the first film electrode 221 and the second film electrode 222. The oxygen concentration of the gas to be measured is obtained by measuring the voltage difference.

Similar to the first embodiment, the supporting body 210 of the second embodiment supports the first ion conductive layer 231. The first ion conductive layer 231 thus can be formed on the supporting body 210 by a thick film or a thin film process. The thickness of the first ion conductive layer 231 is reduced, and sensitivity, thermal shock resistance and operating lifespan of the electrochemistry apparatus 200 is increased.

The supporting body 210 can be formed by a conductive porous metal or a conductive porous ceramic, such as a porous stainless steel, a porous Perovskite conductive ceramic with hominess phase material (tungsten carbide cermet with a zirconium oxide combined ceramic), a Perovskite comprising a conductive ceramic ($LaSrMnO_3$, $LaSrCoO_3$, $LaSrCoFeO_3$) or a combined material having porous metal and conductive ceramic. In a modified embodiment, the supporting body 210 is made of a conductive porous metal to provide a heating function, such that an additional heating element is not required.

When the supporting body 210 is made of non-conductive porous metal, the second ion conductive layer 232 can be omitted.

The first ion conductive layer 231 and the second ion conductive layer 232 are formed by a heat spreading, an immersion plating or a spin coating process. The first ion conductive layer 231 and the second ion conductive layer 232 comprise materials selected from a group of zirconium oxide, cerium oxide, $LaMo_2O_9$, Perovskite and Ga—Mg—Sr—La oxides.

Similar to the first embodiment, the first and second film electrodes 221, 222 can comprise: (a) metal materials such as Pt, Au, Pd, Rh, Ir, Ru, Os, Ni, Co and Fe which can easily electrical-chemical react with oxygen; (b) Perovskite ceramics such as $LaSrMnO_3$ and $LaSrCoFeO_3$, which can easily electrical-chemical react with oxygen; (c) a combined material comprising the metal materials mixed with the Perovskite ceramics mentioned above with zirconium oxide to provide ion-conduction and electron-conduction; and (d) a second phase material for resisting carbonization, poisoning or vulcanization, such as copper or cerium oxide. The first and second film electrodes can be formed by a thick film process, such as a screen print, an injection print or a spread process. The first and second catalyzer layers can also be formed by a thin film process, such as a lift-off method.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An electrochemistry apparatus, comprising
   a supporting body, made of a first material and having a surface; and
   a reaction layer for generating electromotive force, covering the surface of the supporting body, the reaction layer comprising:
   an ion conductive layer, comprising a first surface and a second surface, wherein the first surface is opposite to the second surface, and the ion conductive layer is made of a second material, wherein the second material has a thermal expansion coefficient which approximates the thermal expansion coefficient of the first material, the second material has an ionic conductivity which is greater than the ionic conductivity of the first material, and the first material has a toughness which is greater than the second material;
   a first film electrode, formed on the first surface; and
   a second film electrode, formed on the second surface and located corresponding to the first film electrode;
   wherein the supporting body has a symmetrical shape around a major axis of the supporting body and has a plurality of grooves extending parallel to the major axis, and the grooves are symmetrically located on the surface of the supporting body with respect to the major axis.

2. The electrochemistry apparatus as claimed in claim 1, wherein the first material is selected from a group of zirconium oxide base, zirconium oxide base with $YNbO_4$, zirconium oxide base with aluminum oxide, cerium oxide base with aluminum oxide, Perovskite with aluminum oxide and tungsten carbide cermet with zirconium oxide, and the second material is selected from a group of zirconium oxide doped with positive ion with +2 charges, zirconium oxide doped with positive ion with +3 charges, zirconium oxide co-doped with positive ion with +2 and +3 charges, cerium oxide, $LaMo_2O_9$, Perovskite and Ga—Mg—Sr—La oxides.

3. The electrochemistry apparatus as claimed in claim 1, wherein the first material has a toughness of greater than about 5.1 $Mpa/m^{1/2}$.

4. The electrochemistry apparatus as claimed in claim 1, wherein the first material has a toughness in the range from 5.1 to 18 $Mpa/m^{1/2}$.

5. The electrochemistry apparatus as claimed in claim 1, wherein the second material has an ion conductivity of greater than about 0.015 S/cm at 800° C.

6. The electrochemistry apparatus as claimed in claim 1, wherein the second material has an ion conductivity in the range from 0.015 to 0.022 S/cm at 800° C.

7. The electrochemistry apparatus as claimed in claim 1, wherein the material of both the first film electrode and the second film electrode comprises the second material and a catalyzer.

8. The electrochemistry apparatus as claimed in claim 7, wherein the material of the catalyzer is selected from a group of Pt, Au, Pd, Rh, Ir, Ru, Os, Ni, Co, Fe, $LaSrMnO_3$, $LaSrCoFeO_3$ and the complex thereof.

9. The electrochemistry apparatus as claimed in claim 8, wherein the catalyzer comprises an additive, and the additive is selected from a group of copper and cerium oxide.

10. The electrochemistry apparatus as claimed in claim 1, further comprising a heating wire covering the surface of the supporting body, wherein a ratio of the area covered by the heating wire to the area covered by both the first and the second film electrodes is in the range of 1:1 to 3:1.

11. The electrochemistry apparatus as claimed in claim 1, wherein the material of the heating wire is selected from a group of Pt, Au, Pd, Rh, Ir, Ru, Os, Ni, Co, Fe, $LaSrMnO_3$, $LaSrCoFeO_3$ and the complex thereof.

12. The electrochemistry apparatus as claimed in claim 1, wherein the material of the heating wire comprises an additive, the additive is zirconium oxide.

13. The electrochemistry apparatus as claimed in claim 1, wherein the first film electrode and the second film electrode each are covered by a gas diffusion layer, the material of the gas diffusion layer is selected from a group of $LaAl_{11}O_8$, $LaAlO_3$ and magnesium aluminate spinel.

14. The electrochemistry apparatus as claimed in claim 13, wherein a proportion of $LaAl_{11}O_8$ in the material of the gas diffusion layer is in the range from 50 to 100 mol %.

15. The electrochemistry apparatus as claimed in claim 13, wherein the gas diffusion layer has a void ratio in the range from 20 to 65%.

16. The electrochemistry apparatus as claimed in claim 1, wherein the first material of the supporting body is selected from a group of a conductive porous metal, a conductive porous ceramic and a complex thereof, wherein the conductive porous ceramic is selected from a group of $LaSrMnO_3$, $LaSrCoO_3$, $LaSrCoFeO_3$ and a combined material thereof.

* * * * *